United States Patent [19]

Liebetruth

[11] Patent Number: 4,570,263
[45] Date of Patent: * Feb. 11, 1986

[54] TOMOGRAPHIC X-RAY APPARATUS FOR THE PRODUCTION OF TRANSVERSE LAYER IMAGES

[75] Inventor: Reiner Liebetruth, Erlangen, Fed. Rep. of Germany

[73] Assignee: Siemens Aktiengesellschaft, Berlin & Munich, Fed. Rep. of Germany

[*] Notice: The portion of the term of this patent subsequent to Nov. 13, 1996 has been disclaimed.

[21] Appl. No.: 552,773

[22] Filed: Nov. 17, 1983

Related U.S. Application Data

[63] Continuation of Ser. No. 320,737, Nov. 12, 1981, Pat. No. 4,177,922, which is a continuation of Ser. No. 53,263, Jun. 29, 1979, abandoned, which is a continuation of Ser. No. 775,452, Mar. 8, 1977, Pat. No. 4,174,481.

[30] Foreign Application Priority Data

Mar. 31, 1976 [DE] Fed. Rep. of Germany ....... 2613809

[51] Int. Cl.$^4$ .............................................. G03B 41/16
[52] U.S. Cl. ............................................ 378/20; 378/4
[58] Field of Search ............................ 378/20, 4, 146

[56] References Cited

U.S. PATENT DOCUMENTS

| | | |
|---|---|---|
| 3,101,407 | 8/1963 | Shipman, Jr. . |
| 3,780,291 | 12/1973 | Stein et al. . |
| 3,974,388 | 8/1976 | Distler et al. ................... 250/445 T |
| 4,045,672 | 8/1977 | Watanabe . |
| 4,051,379 | 9/1977 | Zacher ................................... 378/7 |
| 4,174,481 | 11/1979 | Liebetruth ...................... 250/445 T |
| 4,477,922 | 10/1984 | Liebetruth . |

FOREIGN PATENT DOCUMENTS

| | | |
|---|---|---|
| 2237272 | 2/1974 | Fed. Rep. of Germany . |
| 1561969 | 2/1969 | France . |
| 2052548 | 4/1971 | France . |
| 2145325 | 2/1973 | France . |
| 2163959 | 7/1973 | France . |

OTHER PUBLICATIONS

Bowley, et al, "A Radioisotope Scanner for Rectilinear, Arc, Transverse Section and Longitudinal Section Scanning: (ASS–the Aberdeen Section Scanner)" *British Journal of Radiology*, vol. 46, 1973, pp. 262-271.

Norman, et al, "Localization with the EMI Scanner", *American Journal of Radiology*, vol. 125, No. 4, Dec. 1975, pp. 961-964.

Haaga, et al, "CT Longitudinal Scan", *American Journal of Roentgenology*, vol. 127, 1976, pp. 1059-1060.

Kuhl, et al, "Transmission Scanning," *Radiology*, vol. 87, Aug. 1966, pp. 278-284.

*Primary Examiner*—Craig E. Church
*Attorney, Agent, or Firm*—Hill, Van Santen, Steadman & Simpson

[57] ABSTRACT

In an extension of the utility of rotary scan tomographic x-ray apparatus, the apparatus is locked in a fixed angular relationship and the patient support is automatically advanced in small longitudinal increments relative to the angularly fixed scanner, the scanner being pulsed in synchronism with the longitudinal steps to produce successive sets of transmittance readings defining a radiographic shadow image having a substantial longitudinal extent. The stored sets of readings may be reproduced on a conventional television display unit. Advantageously, the scanner may present a fan-type beam which in a fixed angular relationship to the patient still scans a substantial portion of the patient cross section, the x-ray source or sources being pulsed at successive longitudinal positions of the patient relative to the scanning apparatus, and the successive sets of readings being utilized for on line display of a shadow radiograph covering the desired longitudinal extent.

35 Claims, 2 Drawing Figures

Fig.1

TOMOGRAPHIC X-RAY APPARATUS FOR THE PRODUCTION OF TRANSVERSE LAYER IMAGES

CROSS-REFERENCE TO RELATED APPLICATIONS

The present application is a continuation of my pending application U.S. Ser. No. 320,737 filed Nov. 12, 1981, now U.S. Pat. No. 4,177,922 said application Ser. No. 320,737 is a continuation of my pending application U.S. Ser. No. 053,263 filed June 29, 1979; now abandoned said application Ser. No. 053,263 is a continuation of my earlier application U.S. Ser. No. 775,452 filed Mar. 8, 1977, now U.S. Pat. No. 4,174,481 issued Nov. 13, 1979, and the disclosure of said pending application is incorporated herein by reference.

BACKGROUND OF THE INVENTION

This invention relates to a tomographic x-ray apparatus for the production of transverse layer images of an exposed object, consisting of a patient's support, an x-ray measuring arrangement with an x-ray source, which genertes a bundle of x-rays penetrating the exposed object and of which the cross sectional extent perpendicular to the plane of the layer is equal to the thickness of the layer, for example, and a radiation receiver which ascertains the radiation intensity beyond the object by scanning the projected bundle of rays, and a driving device for the measuring arrangement including a pivot mounting for accommodating rotational movements of the x-ray measuring arrangement, the apparatus further including a measurand converter for the conversion of the signal supplied by the radiation receiver into a tomographic image.

For detecting the layer image, the rotational movements may take place through equidistant angular amounts, each in alternating sequence with a displacement of the measuring arrangement along a straight line perpendicular to the central ray of the bundle of x-rays, when a single detector is used as the radiation receiver. Alternatively, it is possible to dispense with the displacements along a straight line path if the radiation receiver is built up of a multiplicity of ray detectors whose signals are simultaneously processed by the measurand converter. For example, the x-ray beam may be fan-shaped and the detectors may be arranged in succession so as to simultaneously receive the x-ray energy after traverse of paths of equal length.

A tomographic x-ray apparatus of this kind is described in U.S. Pat. No. 3,974,388 issued Aug. 10, 1976.

SUMMARY OF THE INVENTION

The invention has for its object to extend the utility of a tomographic x-ray apparatus of the rotary scan type.

In accordance with the invention, this object is achieved by virtue of the fact that there are provided means for producing an automatic step by step displacement of the patient support relative to the measuring arrangement in the longitudinal direction during the synchronized pulsing of the scanner and with storage of the signals supplied by the radiation receiver, the measuring arrangement being locked against rotation, and by virtue of the fact that there is connected to the measurand converter a television display unit for reproducing an x-ray shadow image of the patient, which is computed by the measurand converter from the signals of the radiation receiver over the range of longitudinal displacement. In the tomographic x-ray apparatus according to the invention there is provided with the aid of the radiation receiver an x-ray image which is similar to a conventional radiograph.

Other objects, features and advantages of the present invention will become apparent from the following detailed description taken in conjunction with the accompanying sheet of drawings.

DETAILED DESCRIPTION

Figure 1:
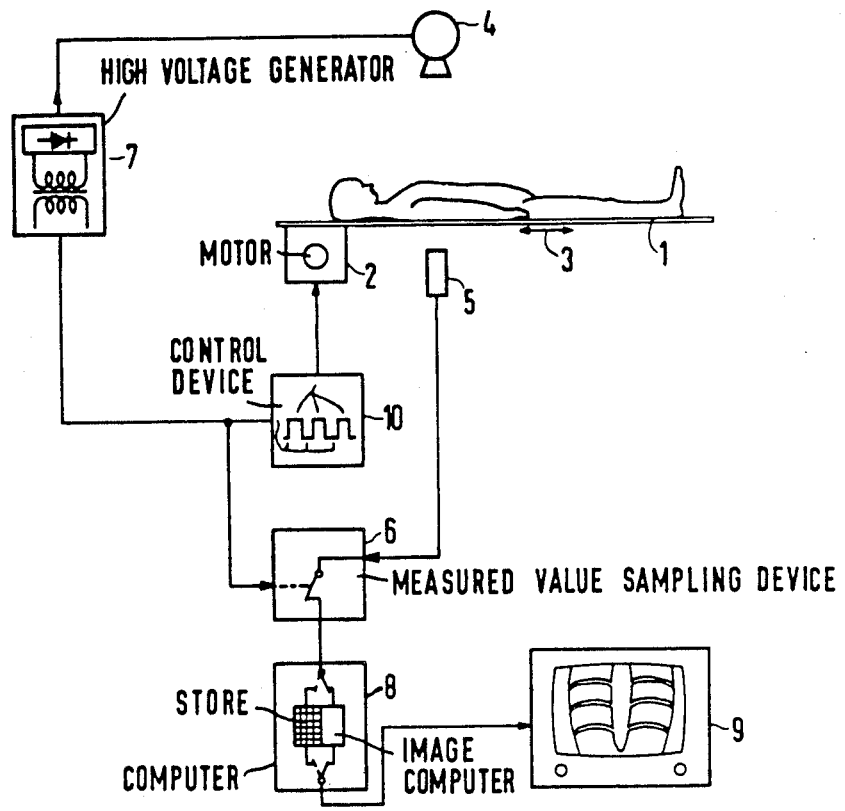
FIG. 1 shows those parts of a tomographic x-ray apparatus according to the invention which constitute the essential apparatus components of the invention and which are utilized in the practice of the inventive method.

In FIG. 1 there is shown a patient's support 1 which is adapted to be subjected to longitudinal reciprocating movement in the direction indicated by double arrow 3 by means of a motor 2. For producing x-ray images, there is provided a measuring arrangement consisting of an x-ray tube 4 and a radiation receiver 5. The output of the radiation receiver 5 is connected to a measurand reading unit 6 so that the analog readings from the radiation receiver 5 can be converted to digital form and stored. The output of the radiation receiver 5 may be sampled by means of the reading unit 6 during intervals corresponding to the intervals of energization of the high voltage generator 7 which supplies the x-ray tube 4. For the sake of diagrammatic illustration, the measured value sampling device 6 is shown as supplying each sample of the readings from the radiation receiver 5 selectively to an image computer component or a "store" component of computer 8. For the case where the measured value sampling device 6 stores the analog readings from receiver 6 in analog form only for the time interval required to convert such analog readings to digital form, during normal tomographic scanning, the digital readings so obtained by means of the sampling device 6 may be supplied to the image computer of component 8 after each energization of the x-ray source 4 for storage in a suitable computer memory. The "store" component for use in producing the longitudinally extensive radiograph may comprise a RAM buffer memory and circulating memory as shown in the tenth figure of an article entitled "The Siretom, a Computerized Transverse Axial Tomograph for Brain Scanning", of which the present applicant is one of the authors, said article being found in the publication *Electromedica*, number 2-3 of 1975, pages 48 through 55. The "store" of component 8 may store each set of readings from receiver 5 corresponding to each patient longitudinal position at a respective row of storage cells so that the rows may be read out in step with the horizontal deflection rate of the television display unit 9.

In addition, FIG. 1 illustrates a control device 10 which controls the longitudinal driving motor 2 and also the measured value sampling device 6 and the high voltage generator 7.

Figure 2:
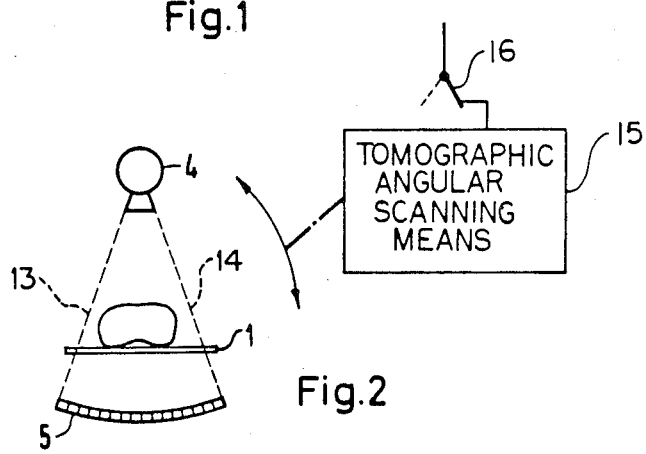
FIG. 2 shows a detail of the tomographic apparatus according to FIG. 1, the view of FIG. 2 being taken in the transverse plane being scanned by the apparatus of FIG. 1.

According to the embodiment of FIG. 2, the measuring arrangement 4, 5 may comprise an x-ray tube 4 which generates a fan-shaped bundle of x-rays having lateral margins as indicated at 13, 14, the x-ray energy being incident upon the radiation receiver 5 which is curved about the focus of the x-ray tube 4. The radiation receiver 5 consists of a detector blank comprising a multiplicity of detector units, for example 242 detectors, so that in the radiation of the patient at a given longitudinal position, 242 individual measurands or readings are obtained. For producing a transverse layer image, the unit 4, 5 is rotated under the control of scanning means 15, FIG. 2, about the patient in a plane perpendicular to the length of the patient support 1 and in the plane of the bundle of rays defined by marginal paths 13, 14 in FIG. 2. The output signals of the radiation receiver 5, which are supplied for each angular position of the measuring arrangement 4, 5, are applied by the measurand-reading unit 6 to the computer 8 which computes therefrom in the known manner a transverse layer image.

In the production of a longitudinally extensive shadowgraph, the unit 4, 5 is restricted to a limited angular relationship, such as the particular single angular relationship indicated in FIG. 2, as by opening switch 16 to disable the angular scanning means 15, FIG. 2, and the patient support 1 is shifted with the patient so as to cover the desired longitudinal extent of the patient. During the longitudinal displacement by means of the motor 2, the x-ray tube 4 is pulsed and the radiation receiver 5 is read for each such x-ray pulse. There is therefore obtained for predetermined longitudinal positions of the patient support 1 relative to the measuring arrangement 4, 5 measurands or readings which characterize the attenuation of the x-radiation in its passage through the patient. The "store" of computer 8 stores the successive sets of readings as a basis for generating an x-ray shadow image when the stored values are reproduced on the display unit 9 as is indicated in FIG. 1.

Each set of readings from the receiver 5 for a given longitudinal position of the patient relative to the apparatus 4, 5 is utilized to produce an image line extending horizontally on the display unit 9. The number of image dots per image line is equal to the number of detectors in the radiation receiver, so that each horizontal line may have a resoltuion of 242 dots for the case where there are 242 individual detectors within the receiver 5 as described with respect to FIG. 2. The frequency of the turn-on pulses supplied by control device 10 to the high voltage generator 6 and the speed of operation of motor 2 in driving the support 1 in the direction of arrow 1 are so correlated to one another that the positional resolution in the longitudinal direction corresponds substantially to that which can be provided by the number of detectors in the radiation receiver 5 with respect to the transverse direction. Thus, the control device 10 may supply a turn-on pulse to the high voltage generator at successive longitudinal positions of the patient support 1 relative to the measurement apparatus 4, 5 which are separated by one millimeter, for example.

It is also possible within the scope of the invention to use a single detector as the radiation receiver instead of a bank of detectors if the unit 4, 5 is so arranged as to be transversely displaceable for each relative longitudinal position of the patient to the unit 4, 5. Where a single detector is utilized for the receiver 5, the readings from the detector for the successive transverse positions would be stored as a set of readings, for example each reading being converted to digital form prior to storage. The successive sets of readings so stored would then represent information with respect to successive longitudinal portions of the patient as in the example using the arrangement of FIG. 2 and would be displayed exactly as shown in FIG. 1.

In the embodiment described with reference to FIG. 2, the pulsing of the x-ray tube 4 takes place with the patient's support 1 in predetermined longitudinal positions, that is to say the successive turn-on pulses are supplied to the x-ray generator 7 from the control device 10 at predetermined longitudinal positions of the patient's support 1.

It is also conceivable within the scope of the invention for the support 1 to be fixedly located and for the measuring arrangement 4, 5 to be arranged to be displaced in the longitudinal direction of the support 1 both for producing a synoptic radiographic picture and for the subsequent selection of a specific longitudinal position relative to the patient for scanning to produce a transverse layer or tomographic image.

The computer 8 comprises a store which stores the signals corresponding to an image line which signals are supplied to the store from the radiation receiver 5 via the measured value sampling device 6. The store may have a series of storage locations for the set of readings corresponding to each longitudinal position of the patient, and the number of such series of storage locations may then correspond to the number of detectors of radiation receiver 5, FIG. 2. Thus, after the successive sets of readings are stored by means of the store component of computer 8, the desired synoptic image can be reproduced on the television display unit 9.

For the reproduction of a synoptic exposure from the store component of computer 8, no actual image computation takes place so that the image computer component of computer 8 is not utilized during the generation of the longitudinally extensive radiographic image. The computer store of component 8 for purposes of generating the radiographic image has a number of image stores which is equal to the number of image lines times the number of image dots per image line. For the example of FIG. 2, as previously mentioned, each image line store may comprise 242 storage cells. For reproducing a synoptic exposure, there takes place at the commencement of the displacement of the support 1 by means of the motor 2 a change-over of the computer input, that is to say a disconnection of the image computer component of computer 8 and a connection of the computer input to the described store component of computer 8. In this case, the display unit 9 is also disconnected from the image computer component of computer 8 and connected to said store component at its input for displaying the radiographic or synoptic image as specifically illustrated in FIG. 1.

The control device 10 is so constructed that it turns on the motor 2 and the x-ray generator 7 pulse-wise. Therefore, the support motor 2 is first turned on or pulsed for carrying out a displacement step of the support 1. For this purpose, the motor 2 may be a conventional stepping motor which indexes a desired longitudinal increment for each pulse supplied thereto. After completion of this longitudinal displacement step, the x-ray tube 4 is turned on by means of the control device 10 supplying a turn-on pulse to the x-ray generator 7 so as to produce an x-ray pulse of desired duration. The support motor 2 then receives a further turn-on pulse for carrying out a further displacement step of the support 1; thereafter, the x-ray tube 4 is turned on by way of the x-ray generator, and so on. The control device 10 thus comprises a simple sequence timer circuit which alternately supplies control pulses to motor 2 and to high voltage generator 7 during the storage of the successive sets of readings from the receiver 5.

The measurand-reading unit 6 is shown as including a switch which connects the output of the radiation receiver 5 to the input of the computer 8 each time it receives at its left-hand input a pulse from the control device 10 signifying that the x-ray tube 4 has been turned on. Thus, a sample of suitable duration of the output from the radiation receiver 5 for each detector shown in FIG. 2, for example, is transmitted to the store of component 8. Of course, the switch of component 6 is of an electronic nature. If the store of component 8 is a digital storage, then component 6 may include a suitable analog accumulator for the respective readings from the detectors and suitable analog to digital circuitry for converting the readings to digital form and supplying them to the store of component 8.

SUPPLEMENTARY DISCUSSION

Simply for the sake of example, the radiation receiver 5 may comprise a row of semiconductor diodes presenting respective generally narrow rectangular edge faces to the impinging radiation, a fluorescent layer being interposed or sandwiched between every two diodes and at the opposite ends of the row of diodes. In such a radiation receiver, the x-radiation strikes the fluorescent layers at the relatively narrow generally rectangular edges thereof and causing each fluorescent layer to emit visible light in one or both lateral directions such that the impinging radiation produces a corresponding current flow in the respective associated semiconductor diodes. A semiconductor x-ray detector of this type is disclosed in German Patent Application P No. 26 22 655.1 filed May 20, 1976 wherein the inventors are the present applicant, Dr. Gunter Luderer and Burghard Weinkauf, such case being identified by the assignee reference number VPA 76 P 5058.

In carrying out the method of the present invention with a semiconductor x-ray detector of the type illustrated in FIG. 2, the support 1 with the patient thereon is placed in an initial position, with the x-ray beam path 13, 14 arranged to impinge at one longitudinal position and the motor 2 set to index the support 1 so as to progressively move the patient support 1 through the scanning region. The measured value sampling device 6 is placed in the operating mode such that the switch of component 6 is normally opened but is closed for a suitable interval in response to each pulse from the control device 10. Similarly, the computer component 8 is switched over so that the computer input is connected with the store of component 8 utilized to provide storage for the successive sets of readings from receiver 5. The control device 10 is now turned on and proceeds to alternately supply control pulses to the generator component 7 and sampling device 6 on the one hand, and to the stepping motor 2 on the other hand. Thus, during each energization of the x-ray source 4, a suitable sample of the readings from the detectors of receiver 5 is stored within the store component of computer 8, whereupon the motor 2 is energized to produce a longitudinal indexing movement, the sampling device 6 and generator 7 then again being pulsed, and so on. When the successive sets of readings from receiver 5 have been stored in this way, the stored values can be processed as described in detail in the aforementioned *Electromedica* article, but in such a manner that each set of stored readings is scanned in synchronism with the line rate of the display device 9 so that each set of readings appears as a horizontal line on the display screen as is illustrated in FIG. 1.

It will be apparent that many modifications and variations may be effected without departing from the scope of the novel concepts and teachings of the present invention.

I claim as my invention:

1. In a tomographic apparatus for the production of transverse-layer images of an exposed subject, having a patient's support, an x-ray measuring arragement including an x-ray source which produces a beam of x-ray energy for penetrating the exposed subject with respect to a transverse plane, and a radiation receiver which provides readings which are measures of the radiation intensity of the transmitted beam, scanning means coupled with the source for rotating at least said source through a wide range of angular relationships with said subject for generating a sufficient number of sets of readings to define a tomographic layer image, the improvement comprising longitudinal drive means operable in a longitudinal scan mode for producing relative longitudinal movement between the measuring arrangement and the patient's support in the longitudinal direction of the support, storage means operable in said longitudinal scan mode for storing readings from the radiation receiver, means for releasably locking said measuring arrangement in a single angular relationship with said subject, control means coupled with the longitudinal drive means and said x-ray source for controlling said longitudinal movement through successive longitudinal positions while the measuring arrangement is locked in said single angular relationship and simultaneously automatically controlling and coordinating operation of said x-ray source for exposing said subject to radiation at each of said successive longitudinal positions and simultaneously automatically controlling said storage means during said longitudinal scan mode for storing sets of readings from the radiation receiver for each successive longitudinal position, and said control means in said longitudinal scan mode effecting storage of said sets of readings relating to successive longitudinal positions for defining in combination an x-ray shadow image of the patient having a substantial transverse extent and having a longitudinal extent corresponding to the range of longitudinal movement produced by said longitudinal drive means during the storage operation.

2. The improvement of claim 1, wherein said measuring arrangement is longitudinally fixed during the longitudinal scan mode and the patient's support is longitudinally driven by said longitudinal drive means.

3. The improvement of claim 1, wherein the radiation receiver consists of a bank of detectors for receiving a fan-shaped x-ray beam, and wherein said control means includes means for turning on the x-ray source only when the measuring arrangement and the patient's support are in successive relative longitudinal positions which are successively offset longitudinally by a longitudinal increment substantially corresponding to the image resolution defined by the number of detectors of said bank.

4. The improvement of claim 1 further comprising a television display means connected to said storage means for reproducing the successive sets of stored readings as successive video lines of an x-ray shadow image of the patient.

5. Tomographic apparatus for the production of transverse-layer images, said apparatus comprising a patient support having a longitudinally extended patient receiving space, x-ray source means for producing a beam of x-ray energy for penetrating the patient receiving space at a transverse plane therein, and radiation receiver means for providing readings which are measures of the radiation intensity of the transmitted beam transmitted through the transverse plane of the patient receiving space, scanning means coupled with the x-ray source means for producing rotational movements of the beam in said transverse plane through a wide range of angular relationships with respect to the patient receiving space so as to generate a sufficient number of sets of said readings for computer construction of a tomographic layer image, longitudinal drive means for producing relative longitudinal movement between the x-ray source means and the patient support in the longitudinal direction of the patient receiving space during storage of the readings from the radiation receiver means, control means coupled with the longitudinal drive means and with said x-ray source means for producing longitudinal movement through successive longitudinal positions while the x-ray beam is restricted to substantially one angular relationship with respect to said patient receiving space so as to scan a patient essentially from only a single direction during said longitudinal movement and for simultaneously automatically coordinating operation of said x-ray source means with said longitudinal movement for generating a plurality of said sets of readings from the radiation receiver, each set in said plurality being with reference to one of said successive longitudinal positions, and means for storing said sets of readings relating to successive longitudinal positions for defining in combination an x-ray shadow image of the patient having a substantial transverse extent and having a longitudinal extent corresponding to the range of longitudinal movement produced by said longitudinal drive means during the storage operation.

6. An apparatus as claimed in claim 5, wherein the x-ray source means is fixedly located during the storing of said sets for the defining of the shadow image, said x-ray source means projecting a flat beam configuration with a thickness corresponding to the thickness of said beam during operation of said scanning means in the production of said computer constructed tomographic layer image, and wherein the patient support is longitudinally driven by said longitudinal drive means.

7. An apparatus as claimed in claim 5, wherein said x-ray source means provides a fan-shaped x-ray beam configuration of restricted longitudinal extent, said control means includes means for turning on the x-ray source means only when the x-ray source means and the patient support are in successive relative longitudinal positions which are successively offset longitudinally by a longitudinal increment generally corresponding to the image resolution defined by the restricted longitudinal extent of said fan-shaped x-ray beam configuration.

8. An apparatus as claimed in claim 5, further comprising reference means at said patient support for locating a patient in a longitudinal direction with a resolution generally corresponding to the incremental longitudinal distance between the successive longitudinal positions where the successive sets of readings are taken, and video display means for reproducing the successive sets of stored readings as successive video lines of an x-ray shadow image of the patient, and providing for the identification of a patient transverse layer to be later scanned with the operation of said scanning means, with an accuracy generally corresponding to the thickness of such patient transverse layer.

9. Tomographic apparatus for the production of transverse layer images, said tomographic apparatus comprising:

a patient support having a longitudinal direction and a longitudinally extended patient receiving space, x-ray source means for producing respective x-ray beams forming a fan-shaped beam configuration for penetrating a patient transverse layer lying in a transverse plane of the patient receiving space, the x-ray beams being directed parallel to the transverse plane, and the cross sectional extent of the beam configuration being restricted longitudinally to a body layer of interest, radiation receiver means for receiving the respective x-ray beams of the fan-shaped beam configuration after transmission along respective laterally offset measurement paths lying in the transverse plane of the patient receiving space and for supplying a set of electrical measurement signals in accordance with the radiation impinging on the radiation receiver means after transmission along the respective laterally offset measurement paths and through the patient transverse layer, and providing a given lateral resolution, measured value sampling means connected with said radiation receiver means for receiving the set of electrical measurement signals from said radiation receiver means and for supplying a set of measurement readings representing sampled values in accordance with the radiation incident on the radiation receiver means during a sampling interval, scanning means coupled with said x-ray source means during a transverse layer scanning operation for producing rotational movement of the beam configuration in said transverse plane through a wide range of angular relationships relative to said patient receiving space so as to direct the beam configuration through the patient layer from a sufficient number of different directions for computer construction of the patient transverse layer for viewing as a transverse-layer image, longitudinal scanning means for producing relative successive incremental longitudinal movement between said fan-shaped beam configuration and the patient support in the longitudinal direction of the latter, control means coupled with the x-ray source means, the measured value sampling means, and with the longitudinal scanning means for operation in an x-ray shadow image generating mode wherein the fan-shaped beam configuration remains in a single angular relationship relative to said patient space for automatically coordinating operation of said x-ray source means and said relative longitudinal movement through a substantial longitudinal distance for generating a shadow image of an extended longitudinal region of a patient in the patient receiving space of the patient support, said control means controlling said measured value sampling means during said operation in said x-ray shadow image generating mode for producing a set of measurement readings for each of said successive increments in the relative longitudinal movement produced by said longitudinal scanning means for defining the shadow image with a sufficient resolution for identification of the longitudinal position of any desired patient transverse layer within the extended longitudinal region of the patient, storage means coupled with the measured value sampling means during said operation in said x-ray shadow image generating mode for storing said successive sets of measurement readings corresponding to the successive increments of said relative longitudinal movement, and display means coupled with said storage means for displaying said successive sets of measurement readings as a visual shadowgraphic image of the extended longitudinal region of a patient with a resolution corresponding with said given lateral resolution of said radiation receiver means.

10. Tomographic apparatus according to claim 9, wherein said x-ray source means provides a fan-shaped beam configuration during a transverse layer scanning operation with a longitudinal extent substantially equal to the thickness of the transverse layer to be computer constructed for viewing as a transverse layer, and said control means controls said measured value sampling means for providing respective sets of measurement readings for successive longitudinal positions which are separated by a distance substantially equal to said given lateral resolution of said radiation receiver means.

11. Tomographic apparatus for the production of transverse-layer images, comprising a patient support, x-ray measuring means including x-ray source means for producing a beam of x-ray energy in a transverse plane for penetrating a patient transverse layer disposed in the transverse plane, radiation measuring means for providing readings in digital form which are measures of the radiation intensity of the transmitted beam, angular scanning means coupled with the x-ray source means for producing rotational movements of the beam in said transverse plane though a wide range of angular relationships relative to said patient transverse layer for generating a sufficient number of sets of readings to define a tomographic layer image, computer means coupled with said radiation measuring means and operable in a tomographic mode for constructing a tomographic layer image based on the sets of readings produced during operation of said angular scanning means, longitudinal scanning means for producing relative longitudinal movement between the beam of x-ray energy and the patient support in the longitudinal direction of the latter during storage by the computer means of the readings from the radiation measuring means, control means coupled with the longitudinal scanning means and with the x-ray source means for producing longitudinal movement while the beam of x-ray energy is restricted from rotation and for simultaneously automatically coordinating operation of said x-ray source means with said longitudinal movement for generating sets of said readings from the radiation measuring means for each of a multiplicity of longitudinal segments of a patient on the patient support, said computer means storing sets of readings relating to successive longitudinal segments for defining in combination an x-ray shadow image of the patient having a substantial transverse extent and having a longitudinal extent corresponding to the range of longitudinal movement produced by said longitudinal scanning means during the storage operation.

12. An apparatus as claimed in claim 11, wherein the x-ray source means is fixedly located during the storage operation for defining the shadow image and the patient support is longitudinally driven by said longitudinal scanning means.

13. An apparatus as claimed in claim 11, wherein said x-ray source means provides a fan-shaped x-ray beam during operation of said longitudinal scanning means, wherein the radiation measuring means comprises a bank of detectors for receiving the fan-shaped x-ray beam, and wherein said control means includes means for turning on the x-ray source means only when the x-ray source means and the patient support are in successive relative longitudinal positions which are successively offset longitudinally by a longitudinal increment substantially corresponding to the image resolution defined by the number of detectors of said bank.

14. An apparatus as claimed in claim 11 further comprising video display means coupled with said computer means for reproducing the successive sets of stored readings relating to successive longitudinal segments as successive video lines of an x-ray shadow image of the patient.

15. The method of aligning a patient with respect to tomographic x-ray apparatus which includes a computer tomographic scanner apparatus for scanning a patient transverse layer from successive angular positions in the plane of the transverse layer for the computer construction of a tomographic image, and which utilizes an x-ray beam having a greatly restricted longitudinal extent according to the thickness of the patient transverse layer to be scanned, said method comprising:

(a) locking said x-ray beam at a single angular relationship with said patient, (b) generating relative successive incremental longitudinal movement between said x-ray beam and said patient, (c) longitudinally scanning said patient by automatically coordinating operation of said x-ray beam with said longitudinal movement by turning on the x-ray beam only once at each longitudinal position so as to effect only one x-ray exposure of each longitudinal segment of the patient for generating a shadowgraphic scanning of the patient with a longitudinal resolution for subsequent positioning of the patient for scanning of a patient transverse layer, (d) displaying sets of readings from the scanner apparatus for the successive longitudinal segments wherein the sets of readings are the basis for successive video lines of varying visual characteristics on the display for in combination providing a general radiographic view representing a longitudinally extensive image, and (e) re-positioning the patient relative to the tomographic x-ray apparatus for a subsequent computer tomographic scanning of a patient transverse layer having said greatly restricted longitudinal extent.

16. The method of claim 17 comprising the additional steps of providing a measure of the patient position relative to the tomographic scanner apparatus during the longitudinal scanning of the patient with a measurement system having a resolution capability corresponding to the lateral resolution of the computer tomographic scanner apparatus, correlating the measurement system with the general radiographic view provided by displaying the sets of readings for locating a desired longitudinal segment of the patient for scanning by the computer tomographic scanner apparatus, and utilizing the correlating step for said re-positioning of the patient relative to said computer tomographic scanner apparatus for subsequent scanning of a patient transverse layer at the desired longitudinal segment.

17. Tomographic apparatus for the production of transverse layer images, said tomographic apparatus comprising:
a patient support having a longitudinal direction and a longitudinally extended patient receiving space,
x-ray source means for producing respective x-ray beams forming a beam configuration for penetrating a patient transverse layer lying in a transverse plane of the patient receiving space, the x-ray beams being directed parallel to the transverse plane, and the cross sectional extent of the beam configuration being equal to the thickness of the patient transverse layer to be scanned thereby,
radiation receiver means for receiving the respective x-ray beams of the beam configuration after transmission along respective laterally offset measurement paths lying in the transverse plane of the patient receiving space and for supplying a set of electrical measurement signals in accordance with the radiation impinging on the radiation receiver means after transmission along the respective laterally offset measurement paths and through the patient transverse layer,
measured value sampling means connected with said radiation receiver means for receiving the set of electrical measurement signals from said radiation receiver means and for supplying a set of measurement readings representing sampled values in accordance with the radiation incident on the radiation receiver means during a sampling interval,
scanning means coupled with said x-ray source means during a transverse layer scanning operation for producing rotational movement of the beam configuration in said transverse plane through a wide range of angular relationships relative to said patient receiving space for directing the beam configuration through the patient layer from a sufficient number of different directions for computer construction of the patient transverse layer for viewing as a transverse-layer image,
longitudinal scanning means for producing relative longitudinal movement between the x-ray source means and the patient support in the longitudinal direction of the support,
control means coupled with the longitudinal scanning means, with the measured value sampling means, and with the x-ray source means for effecting operation in an x-ray shadow image generating mode wherein the x-ray source means remains in a single angular relationship relative to said patient space while the longitudinal scanning means produces longitudinal movement through successive increments comprising a substantial longitudinal distance and simultaneously automatically controlling operation of said x-ray source means for generating a shadow image of an extended longitudinal segment of a patient in the patient receiving space of the patient support,
said control means controlling said measured value sampling means during said operation in said x-ray shadow image generating mode for producing a set of measurement readings for each of said succession of increments in the relative longitudinal movement produced by said longitudinal scanning means for defining the shadow image with a sufficient resolution to enable substantially precise identification of the longitudinal position of any desired patient transverse layer within the extended longitudinal segment of the patient,
storage means coupled with the measured value sampling means during said operation in said x-ray shadow image generating mode for storing successive sets of measurement readings corresponding to the successive increments of said relative longitudinal movement, and
display means coupled with said storage means for displaying said successive sets of measurement readings as a visual shadowgraphic image of the extended longitudinal segment of a patient with a sufficient resolution so that any desired patient transverse layer within the extended longitudinal segment can be substantially precisely identified as to its location within the longitudinal segment.

18. Tomographic apparatus as claimed in claim 17, wherein
said x-ray source means produces a beam configuration during said transverse layer scanning operation with a longitudinal extent substantially equal to the thickness of the transverse layer to be computer constructed for viewing as a transverse layer image, and
said control means controls said measured value sampling means for providing respective sets of said measurement readings for successive longitudinal positions which are separated by a distance generally equal to said longitudinal extent of said beam configuration.

19. Tomographic apparatus for the production of transverse-layer images, said apparatus comprising a patient support having a longitudinally extended patient receiving space, x-ray source means for producing a beam of x-ray energy with a central ray axis for penetrating the patient receiving space at a transverse plane therein, radiation receiver means for providing readings which are measures of the radiation intensity of the transmitted beam transmitted though the transverse plane of the patient receiving space, angular scanning means coupled with the x-ray source means and operable in a computer tomography mode for producing rotational movements of the beam in said transverse plane through a wide range of angular relationships with respect to the patient receiving space so as to generate a sufficient number of sets of readings to provide for computer construction of a tomographic layer image, longitudinal scanning means for producing relative successive incremental longitudinal movement between said central ray axis of the x-ray source means and the patient support in the longitudinal direction of the patient receiving space during storage of the readings from the radiation receiver means, control means coupled to said longitudinal scanning means and to said x-ray source means operable in a shadowgraphic scanning mode during relative longitudinal movement of said centray ray axis through successive longitudinal positions for automatically selectively activating said x-ray source means coordinated with said longitudinal movement while the central ray axis has substantially only one angular relationship with respect to said patient receiving space so as to scan a patient substantially from a single direction during said relative longitudinal movement for generating sets of readings from the radiation receiver means for each successive longitudinal position, and means for storing sets of readings relating to successive longitudinal positions for defining in combination an x-ray shadow image of the patient having a substantial transverse extent and having a longitudinal extent corresponding to the range of longitudinal movement produced by said longitudinal scanning means during the storage operation.

20. Apparatus as claimed in claim 19, wherein the x-ray source means is fixedly located during operation in said shadowgraphic scanning mode such that said central ray axis has the same position relative to said x-ray source means as during operation in said computer tomography mode.

21. Apparatus as claimed in claim 19, wherein said x-ray source means provides a fan-shaped x-ray beam configuration of restricted longitudinal extent with said central ray axis directed centrally thereof, and wherein said control means includes means for turning on the x-ray source means only when the x-ray source means and the patient support are in successive relative longitudinal positions which are successively offset longitudinally by a longitudinal increment substantially corresponding to the lateral image resolution given by the radiation receiver means during operation in said computer tomography mode.

22. Apparatus as claimed in claim 19, further comprising reference means on said patient support for locating a patient in a longitudinal direction with a resolution generally corresponding to the lateral image resolution given by the radiation receiver means during operation in said computer tomography mode, and video display means for reproducing the successive sets of stored readings as successive video lines of an x-ray shadow image of the patient for identification of a patient transverse layer to be later scanned in said computer tomography mode with the operation of said angular scanning means, with an accuracy generally corresponding to the lateral image resolution of said radiation receiver means.

23. The method of aligning a patient with respect to computer tomographic x-ray apparatus which includes an x-ray tomographic scanner apparatus for scanning a patient transverse layer from a multiplicity of successive incremental angular positions about said layer so as to provide a computer constructed tomographic image thereof, and comprising:
  (a) moving a patient longitudinally relative to the scanner apparatus and activating the apparatus to provide pulses of the x-ray energy only for beam paths whose central rays are substantially restricted to one direction with respect to the patient, such that beams of x-ray energy impinge on the patient at successive longitudinal positions offset from each other longitudinally of the patient and such that the exposure of the patient to x-ray energy at each longitudinal position is substantially less than the exposure for a multiple beam position tomographic scanning cycle covering a similar longitudinal segment of the patient, and
  (b) storing respective sets of readings from the scanner apparatus for a given direction of the central rays and for the successive longitudinal positions to provide the data for a graphic display wherein the sets of readings are the basis for successive lines of varying visual characteristics on the display, the stored sets of readings defining a general radiographic view representing a longitudinally extensive image useful in the precise positioning of the patient relative to the central ray axis of the tomographic x-ray apparatus for the purpose of a subsequent scanning where readings from the scanner apparatus are produced at successive incremental angular positions about a transverse layer.

24. The method of claim 23 wherein a patient is positionable with a resolution substantially corresponding to the lateral resolution of the scanner apparatus during computer tomography, said method further comprising the step of displaying a general radiographic view based on the stored sets of readings with a resolution facilitating location of a desired patient transverse layer on the radiographic view.

25. The method of claim 24 comprising the additional step of utilizing the radiographic view for accurate positioning of the patient relative to said central ray axis for scanning of said desired patient transverse layer.

26. Tomographic apparatus for the production of transverse-layer images, comprising a patient support x-ray measuring means including x-ray source means for producing a beam of x-ray energy with a central plane and a beam axis in the central plane, said beam being restricted to a patient transverse layer disposed in the central plane, radiation measuring means for providing readings in digital form which are measures of the radiation intensity of the transmitted beam, angular scanning means coupled with the x-ray source means for producing rotational movements of the beam in said central plane through a wide range of angular relationships relative to said patient transverse layer during tomographic scanning thereof for generating sufficient number of sets of readings to define a tomographic layer image, computer means coupled with said radiation measuring means and operable in a tomographic mode for constructing a tomographic layer image based on the sets of readings produced during operation of said angular scanning means, longitudinal scanning means for producing relative successive incremental longitudinal movement between the beam of x-ray energy and the patient support in the longitudinal direction of the latter during storage by the computer means of the readings from the radiation measuring means, control means coupled to said x-ray source means and said longitudinal scanning means operable in a shadowgraphic scanning mode during relative longitudinal movement of the beam of x-ray energy for pulsing the x-ray source means while the beam axis is in substantially only one angular relationship to the patient support automatically coordinated with said longitudinal movement for generating sets of readings from the radiation measuring means for each of a multiplicity of longitudinal segements of a patient on the patient support with substantially less x-ray exposure of each longitudinal segment than is produced by the multiple projection tomographic scanning of such longitudinal segment, said computer means storing sets of readings relating to successive longitudinal segments for defining in combination an x-ray shadow image of the patient having a substantial transverse extent and having a longitudinal extent corresponding to the range of longitudinal movement produced by said longitudinal scanning means during the storage operation.

27. Apparatus as claimed in claim 26, wherein said x-ray source means provides a common fan-shaped x-ray beam configuration during operation of said longitudinal scanning means and of said angular scanning means, wherein the radiation measuring means comprised a bank of detectors for receiving the fan-shaped x-ray beam, and wherein said control means includes means for turning on the x-ray source means only when the x-ray source means and the patient support are in successive relative longitudinal positions which are successively offset longitudinally by a longitudinal increment substantially corresponding to the image resolution defined by the number of detectors of said bank.

28. Apparatus as claimed in claim 25, further comprising video display means coupled with said computer means for reproducing the successive sets of stored readings relating to successive longitudinal segments as successive video lines of an x-ray shadow image of the patient.

29. Apparatus as claimed in claim 26, wherein the x-ray source means is fixedly located during the storage operation for the defining of the shadow image with its beam axis in the same central plane as during a tomographic mode of operation and wherein the patient support is longitudinally driven by means of said longitudinal scanning means during said shadowgraphic scanning mode and during subsequent positioning of a patient with the assistance of the x-ray shadow image for a subsequent tomographic scanning of a selected patient transverse layer.

30. The method of aligning a patient with respect to tomographic x-ray apparatus which includes a computer tomographic scanner apparatus for scanning a patient transverse layer from successive angular positions in the plane of the transverse layer for the computer construction of a tomographic image, and which utilizes an x-ray beam having a longitudinal extent equal to the thickness of the patient transverse layer to be scanned, said method comprising:
(a) longitudinally scanning a patient by means of said x-ray beam of said scanner apparatus while the beam is substantially restricted to one angular relationship such that the patient is scanned substantially from the one angular relationship only but at successive longitudinal segments of the patient offset from each other longitudinally of the patient, and
(b) displaying sets of readings from the scanner apparatus for the successive longitudinal segments to provide a graphic display wherein the sets of readings are the basis for successive lines of varying visual characteristics on the display, the displayed sets of readings providing a general radiographic view representing a longitudinally extensive image useful in the precise positioning of the patient relative to the tomographic x-ray apparatus for the purpose of a subsequent scanning not restricted to the angular relationship but relating to a patient transverse layer having greatly restricted longitudinal extent.

31. A method as claimed in claim 30 wherein a measurement system having a resolution capability corresponding to the restricted longitudinal extent of a patient transverse layer to be scanned is correlated with the patient position relative to the tomographic scanner apparatus during the longitudinal scanning of the patient, said method comprising the additional step of correlating the measurement system with the general radiographic view provided by the displaying of the sets of readings so as to identify a desired longitudinal segment of the patient for scanning by the computer tomographic scanner apparatus.

32. A method as claimed in claim 31 comprising the additional step of utilizing the correlating step for positioning the patient relative to said computer tomographic scanner apparatus for subsequent scanning of a patient transverse layer at said desired longitudinal segment.

33. The method of aligning a patient with respect to tomographic x-ray apparatus which includes an x-ray tomographic scanner apparatus for scanning a patient transverse layer with a fan-shaped x-ray beam from successive angular positions about said layer so as to provide a computer constructed tomographic image thereof, said method comprising:
(a) moving a patient longitudinally relative to the scanner apparatus,
(b) simultaneously automatically sequentially activating said beam such that the patient is scanned from substantially one angular relationship only but at successive longitudinal positions offset from each other longitudinally of the patient,
(c) storing respective sets of readings from the scanner apparatus for the successive longitudinal positions, and
(d) generating a graphic display wherein the sets of readings are the basis for successive lines of varying visual characteristics on the display, the stored sets of readings defining in combination a general radiographic view representing a longitudinally extensive image of the patient.

34. The method of claim 33 wherein the step of moving said patient is further defined by positioning said patient at selected longitudinal positions for obtaining a resolution substantially corresponding to the longitudinal extent of a patient transverse layer, and wherein the step of generating said graphic display is further defined by displaying said general radiographic view based on the stored sets of readings with a resolution such hat any desired patient transverse layer can be identified on the radiographic view.

35. The method of claim 34 comprising the additional step of utilizing the radiographic view for accurate positioning of the patient for scanning of said desired patient transverse layer.

* * * * *